(12) United States Patent
Chaumat

(10) Patent No.: US 7,572,410 B2
(45) Date of Patent: Aug. 11, 2009

(54) CORE SAMPLING DEVICE INTENDED TO ASSEMBLE TISSUE ARRAYS

(75) Inventor: Pierre Chaumat, Plaisir (FR)

(73) Assignee: Alphelys, Plaisir (FR)

( * ) Notice: Subject to any disclaimer, the term of this patent is extended or adjusted under 35 U.S.C. 154(b) by 634 days.

(21) Appl. No.: 11/281,537

(22) Filed: Nov. 18, 2005

(65) Prior Publication Data

US 2006/0121596 A1   Jun. 8, 2006

(30) Foreign Application Priority Data

Dec. 2, 2004   (FR)   ................................. 04 12776

(51) Int. Cl.
  *B01L 3/00* (2006.01)
  *A61B 10/00* (2006.01)
  *G01N 21/00* (2006.01)
  *G01N 15/06* (2006.01)
  *A01N 1/00* (2006.01)
  *A01N 1/02* (2006.01)
  *C12M 3/00* (2006.01)
  *C12M 1/26* (2006.01)

(52) U.S. Cl. .................... 422/99; 600/566; 600/567; 422/63; 422/68.1; 435/286.2; 435/286.3; 435/284.1; 435/307.1; 435/309.1

(58) Field of Classification Search .................. 422/63, 422/68.1, 99; 435/283.1, 284.1, 286.2, 286.3, 435/307.1, 309.1, 40.5; 600/562, 566, 567
See application file for complete search history.

(56) References Cited

U.S. PATENT DOCUMENTS

| | | | |
|---|---|---|---|
| 6,103,518 A | 8/2000 | Leighton | |
| 6,238,355 B1 | 5/2001 | Daum | |
| 2002/0146813 A1 | 10/2002 | Leighton | |
| 2003/0017446 A1 | 1/2003 | Chasse et al. | |

FOREIGN PATENT DOCUMENTS

WO   WO 03/010280 A1   2/2003

*Primary Examiner*—Tony G Soohoo
*Assistant Examiner*—Dean Kwak
(74) *Attorney, Agent, or Firm*—Oliff & Berridge, PLC

(57) ABSTRACT

A core sampling device includes a core sampling punch, a core excision punch that makes a recess in a receiver body, and an ejector that expels a sample core into the receiver body. The core excision punch is mounted inside the core sampling punch and is substantially coaxial with the core sampling punch. Both punches are able to move in translation and/or rotation with respect to one another, and the ejector is arranged so as to expel cores from each punch.

11 Claims, 2 Drawing Sheets

CORE SAMPLING DEVICE INTENDED TO ASSEMBLE TISSUE ARRAYS

BACKGROUND OF THE INVENTION

1. Field of the Invention

The technical scope of the present invention is that of techniques to produce tissue arrays.

2. Description of the Related Art

The tissue array is a technique to mount sections of biological tissues onto microscope slides for their future visual or electronic analysis. The tissue array technique enables a large number of tissue sections to be mounted onto the same slide contrary to the technique traditionally practiced in pathology laboratories where only one to three sections may be mounted together.

The tissue array techniques consist in taking one or several cores from several dozen, or even several hundred, different blocks containing tissue samples either embedded in paraffin or frozen. All the cores are then assembled in a paraffin block or in a frozen inclusion milieu in which recesses have been made.

The tissue array technique is well known and requires no further description here.

Reference may be made, for example, to patent U.S. Pat. No. 6,103,518 which describes a core sampling device. The embodiment proposed is complicated and based on an arm that is pivoted to successively bring into a working position two sampling punches. The rotation of one punch to the other requires the perfect alignment of the two punches above the core sampling position. Moreover, the position of the donor block support platform must be modified at every operation thereby making the use of such a device both slow and cumbersome.

SUMMARY OF THE INVENTION

The aim of the present invention is to supply a core sampling device that is of simple design, easy to implement by the user and which overcomes the above drawbacks.

The invention thus relates to a core sampling device intended to assemble tissue arrays of the type incorporating a core excision punch intended to make recesses in one or several so-called receiver blocks, a core sampling punch and means to expel the sample cores into one or several paraffin receiver blocks or into any frozen milieu or not, characterized by the fact that the core excision punch is mounted substantially coaxially in the core sampling punch, the sampling punch being in the external position, both punches being able to move in translation and/or rotation with respect to one another, and the ejection means being arranged so as to expel the cores from each punch.

According to one characteristic of the invention, the ejection means are positioned in the sampling punch.

According to another characteristic of the invention, the ejection means are in the form of a rod.

According to yet another characteristic of the invention, the external diameter of the rod is close to the internal diameter of the sampling punch.

According to yet another characteristic of the invention, the punches and ejection means are able to move in translation and in rotation independently of one another.

According to yet another characteristic of the invention, the internal diameter of the external diameter of the core extracted from the donor block.

According to yet another characteristic of the invention, the sampling punch has an internal diameter that substantially corresponds to the external diameter of the core extracted from the receiver block.

According to yet another characteristic of the invention, the punches have a sharp edge intended to facilitate their penetration into the paraffin or the frozen block as well as to facilitate the extraction of the cores.

According to yet another characteristic of the invention, the device comprises an optical system and a first software interface enabling the core extraction positions to be parametered on a donor block, a second software interface to parameter the core positions on the receiver block or blocks, and a positive identification system for the donor and receiver blocks.

A first advantage of the device according to the invention lies in the fact that it enables the pathologists to study a large number of patients simultaneously with a restricted budget and within a limited lapse of time. This thus enables a great acceleration in the progress of research knowledge into new prognostic and diagnostic methodologies, and thus into new treatments.

BRIEF DESCRIPTION OF THE DRAWINGS

Other characteristics, particulars and advantages of the invention will become more apparent from the description given hereafter by way of illustration and in reference to the drawings, in which.

DETAILED DESCRIPTION OF THE PREFERRED EMBODIMENTS

Figure 1:
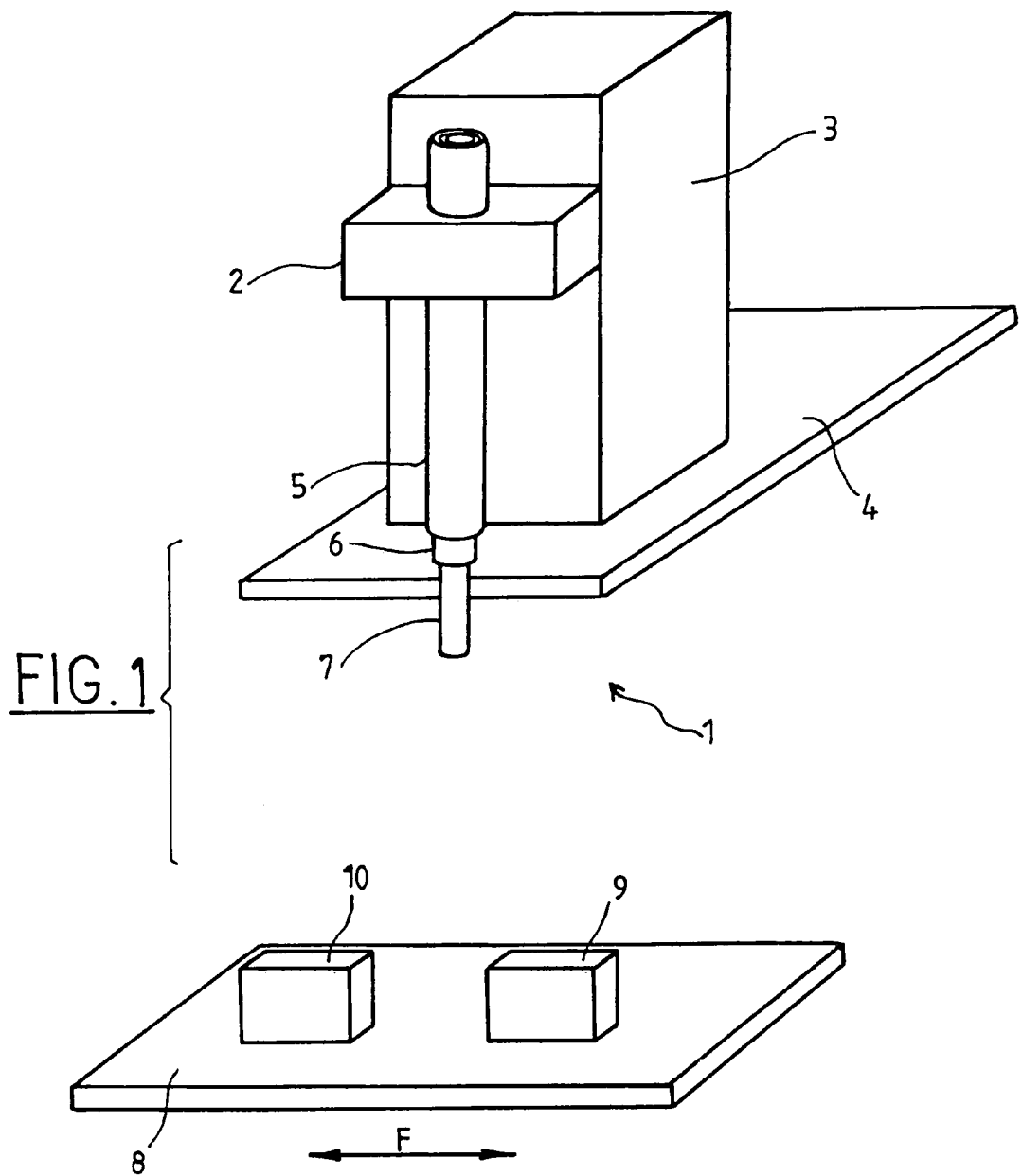
FIG. 1 shows a schematic view of the device according to the invention.
Figure 2:
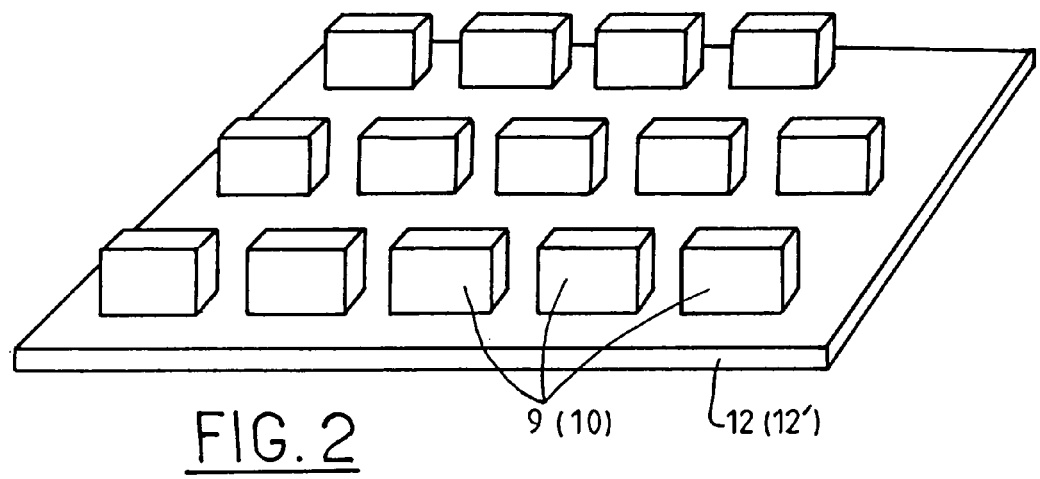
FIG. 2 shows an example embodiment of the block support platform.
Figure 3:
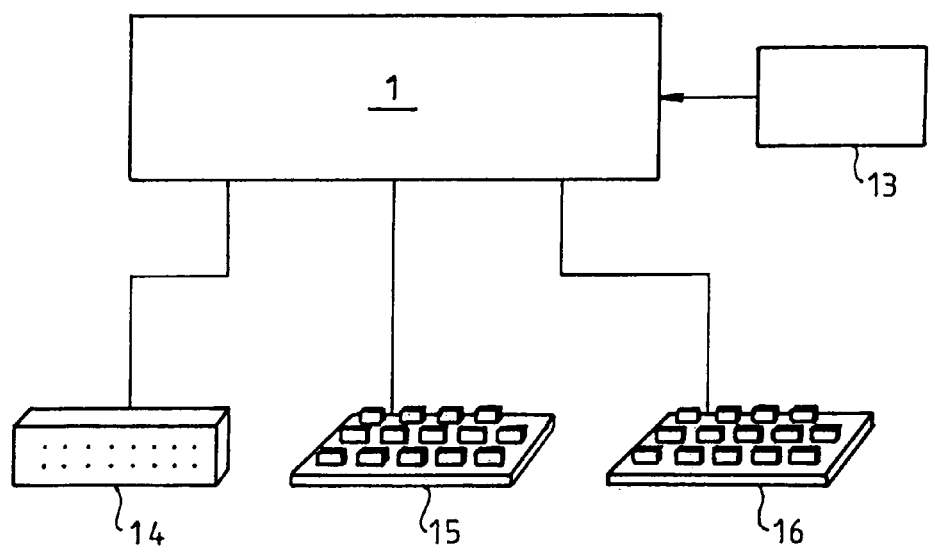
FIG. 3 shows an example embodiment of a core extraction system.

FIG. 1 shows a core extraction device 1 mounted on a support 2 itself integral with a frame 3 fixed onto a support plate 4 intended to support all the elements required for the operation of the device, such as a hydraulic or electrical power unit required to control the different elements, as will be explained hereafter. It classically incorporates a core extraction punch 6 and a core sampling punch 5.

According to the invention, these two punches 5 and 6 are arranged aligned along the same longitudinal axis and defining an inner punch and an outer punch. For the rest of the description, the terms external punch 5 and internal punch 6 will be used. The support 2 receives the external punch 5, the internal punch 6 and an ejector 7. These three parts are mounted aligned along the same axis and able to slide with respect to one another. Punches 5 and 6 are in the form of two tubes, internal punch 6 being inserted in external punch 5. These two punches slide forwards and backwards independently of one another. The ejector 7 is in the form of a solid cylindrical part inserted into the internal punch. Together, these three parts constitute a compact assembly providing all the functionalities of the device 1. Moreover, these three parts are made mobile either manually using toothed bars or by means of the hydraulic unit mentioned previously.

FIG. 1 also shows a support plate 8 on which two core extraction blocks 9 and 10 have been positioned. Block 9 is constituted, for example, by a sample of tissues from which core samples are to be extracted. This block 9 will be termed donor block. Block 10 is a blank block intended to receive the sample cores taken from different donor blocks. block 10 will be termed receiver block. These two blocks are classically blocks of paraffin or frozen blocks.

Advantageously, the support 2 may be mobile and the block plates immobile, or vice versa.

The core extraction device 1 according to the invention is used in the following manner. Naturally, the device 1 is preferentially used in the vertical position as shown in the plane of FIG. 1.

Firstly, the ejector 7 and external punch 5 are made to retract so as to partially free the internal punch 6. The receiver block 10 is brought into a precise position using a classical reference guide system. Firstly, a core is removed from the receiver block 10 using the internal punch 6 to provide a recess into which the tissue sample can be inserted. During this phase, the external punch 5 and the ejector 7 are completely retracted, as indicated above.

The internal punch 6 is made to rotate so as to expel the core taken from the receiver block. This rotation breaks the base of the core which is then able to be removed without difficulty. The core is eliminated by sliding the ejector 7 into the internal punch 6.

A sample core is then taken from a donor block 9 using the external punch 5 by bringing this block perpendicular to the punches. To do this, the internal punch 6 and the ejector 7 are fully retracted manually towards the support 2 using a toothed bar or automatically using a hydraulic or electric unit. The core sample is removed from the donor block 9 by rotating the external punch 5.

The core sample taken from the donor block 9 is transferred into the receiver block 10 once this has been brought back into the position initially referenced by making the recess previously obtained correspond with the position of the external punch 5. The core sample taken from the donor block 9 is then transferred into this recess by sliding the ejector 7 and the internal punch 6 in the external punch 5.

By controlling the height at which the ejector 7 stops, the depth at which the core is introduced into the recess is determined.

This sequence of operations is repeated as often as necessary to obtain the required number of core samples in the receiver block 10 by using different donor blocks 9.

Advantageously, the core extraction device 1 according to the invention is included into an assembly, not shown here, which enables the motorization of the translational and rotational movements of punches 5 and 6 and of the ejector 7, and of the positioning of the punches above the donor and receiver blocks.

This appliance, normally called a tissue arrayer, enables tissue arrays to be built up from donor blocks embedded in paraffin, or from frozen blocks. In the latter case, the punches are themselves refrigerated to preserve the frozen state of the cores during their extraction and transfer.

Its structure may be of the following type.

According to one embodiment, the appliance 1 incorporates a support plate 12 intended to support the donor blocks 9 and a second support plate 12' intended to support the receiver blocks 10. These plates 12 and 12' may be removed from the appliance 1 so as to be loaded up with donor and receiver blocks. The appliance 1 may also incorporate a platform incorporating positioning means for the support plates. This platform may integrate one or several positions for the donor blocks according to the capacity required by the user. Each position incorporates a refrigeration system to keep the donor and receiver blocks frozen during the construction of frozen tissue arrays if using frozen blocks.

The appliance comprises a core extraction device such as that described previously placed on a motor assembly enabling its movement to the nearest micron along the three axes in space so as to place the core extraction system in precise and parametered positions above the donor and receiver blocks. The motorization also enables the separate rotation of each punch, as well as the sliding of each punch and of the ejector.

The appliance may also comprise an optical system 13 and a first software interface 14 enabling the core extraction position or positions to be parametered on the donor block, and a second software interface 15 to enable the position of the cores to be parametered on the receiver block or blocks.

The appliance may integrate a positive identification system 16 for the donor and receiver blocks before each core extraction operation (scanning of barcodes, magnetic codes, etc.) to avoid any error.

It may also comprise a system to detect the sample and the length of the cores and associated error management.

Lastly, it may be enclosed in a enclosed space so as to prevent users from interfering with the movements of the sampling system and to protect the samples during these operations and keep them in a dry atmosphere to avoid the formation of condensation and frost on the blocks, the structures and the punches in the case of tissue arrays being constructed from frozen donor blocks.

What is claimed is:

1. A core sampling device comprising:
   a core excision punch that makes a recess by extracting a core from a receiver body;
   a core sampling punch that extracts a sample core from a sample;
   an ejector that expels the sample core into the receiver body, wherein said core excision punch is mounted inside said core sampling punch and is substantially coaxial with said core sampling punch, both said punches being able to move in translation and/or rotation with respect to one another, and said ejector being arranged so as to expel said cores from each said punch; and
   a positioning assembly that positions the punches above the sample and receiver body so that the sample core taken from the sample may be transferred to the receiver body.

2. Device according to claim 1, wherein said ejector is positioned inside said core excision punch.

3. Device according to claim 2, wherein said ejector is in the form of a rod.

4. Device according to claim 3, wherein the external diameter of said rod is close to the internal diameter of said core excision punch.

5. Device according to claim 2, wherein said punches each have a sharp edge that facilitates their penetration into said receiver body and facilitates the extraction of said cores.

6. Device according to claim 2, wherein said punches and said ejector are able to move in translation and in rotation independently of one another.

7. Device according to claim 1, wherein said punches and said ejector are able to move in translation and in rotation independently of one another.

8. Device according to claim 1, wherein the internal diameter of said core sampling punch substantially corresponds to the external diameter of said sample core, which is extracted from a donor block.

9. Device according to claim 1, wherein said core excision punch has an internal diameter that substantially corresponds to the external diameter of said core extracted from said receiver body.

10. Device according to claim 1, further comprising an optical system and a first software interface enabling the core extraction positions to be parametered on a donor block, a second software interface to parameter said core positions on said receiver body, and a positive identification system for said donor block and receiver body.

11. A method of assembling a tissue array using the core sampling device of claim 1, the method comprising:

making a recess in a receiver body by pressing the core excision punch into the receiver body, and extracting an excised core by retracting the core excision punch, expelling the excised core from the core excision punch by moving the ejector relative to the core excision punch, obtaining a sample core by pressing the core sampling punch into a sample, and extracting the sample core by retracting the core sampling punch, and expelling the sample core into the recess of the receiver body by moving the ejector relative to the core sampling punch.

\* \* \* \* \*